United States Patent
Huh et al.

(10) Patent No.: US 10,054,547 B2
(45) Date of Patent: Aug. 21, 2018

(54) INTEGRAL LABEL-FREE BIOSENSOR AND ANALYSIS METHOD USING THE SAME

(71) Applicant: Electronics and Telecommunications Research Institute, Daejeon (KR)

(72) Inventors: Chul Huh, Daejeon (KR); Sang Hyeob Kim, Daejeon (KR); Byoung Jun Park, Iksan (KR); Eun Hye Jang, Sejong (KR); Myung Ae Chung, Daejeon (KR)

(73) Assignee: ELECTRONICS AND TELECOMMUNICATIONS RESEARCH INSTITUTE, Daejeon (KR)

( * ) Notice: Subject to any disclaimer, the term of this patent is extended or adjusted under 35 U.S.C. 154(b) by 938 days.

(21) Appl. No.: 14/523,462

(22) Filed: Oct. 24, 2014

(65) Prior Publication Data

US 2015/0140680 A1 May 21, 2015

(30) Foreign Application Priority Data

Nov. 18, 2013 (KR) .......... 10-2013-0140105
Mar. 20, 2014 (KR) .......... 10-2014-0032779

(51) Int. Cl.
*G01N 21/75* (2006.01)
*G01N 21/77* (2006.01)

(52) U.S. Cl.
CPC ....... *G01N 21/75* (2013.01); *G01N 2021/757* (2013.01); *G01N 2021/7783* (2013.01); *G01N 2201/061* (2013.01); *G01N 2201/08* (2013.01)

(58) Field of Classification Search
None
See application file for complete search history.

(56) References Cited

U.S. PATENT DOCUMENTS

| 6,990,259 B2 | 1/2006 | Cunningham |
| 7,274,835 B2 | 9/2007 | Panepucci et al. |
| 2011/0129846 A1 | 6/2011 | Huh et al. |

FOREIGN PATENT DOCUMENTS

KR 10-1242138 B1 3/2013

OTHER PUBLICATIONS

Misiakos et al., Monolithically Integrated Frequency-Resolved Zehnder Interferometers for Highly-sensitive Multiplexed Label-free Bio/Chemical Sensing, Sensors 2011 IEEE, Conference dates Oct. 28-31, 2011. (Year: 2011).*
Konstantinos Misiakos et al., "A Monolithic Silicon Optoelectronic Transducer as a Real-Time Affinity Biosensor", Analytical Chemistry, Mar. 1, 2004, pp. 1366-1373, vol. 76, No. 5.

\* cited by examiner

*Primary Examiner* — Rebecca L Martinez

(57) ABSTRACT

Disclosed is an integral label-free biosensor capable of analyzing a biomolecule with high sensitivity by integrating a light source, a photodetector, an optical waveguide, and a microcantilever on a substrate, and a method of detecting a bio-antigen by using the same. The integral label-free biosensor according to the present invention may be manufactured with low cost, be easily integrated with a silicon electron device, and detect a biomolecule with high sensitivity by using a label-free method.

20 Claims, 3 Drawing Sheets

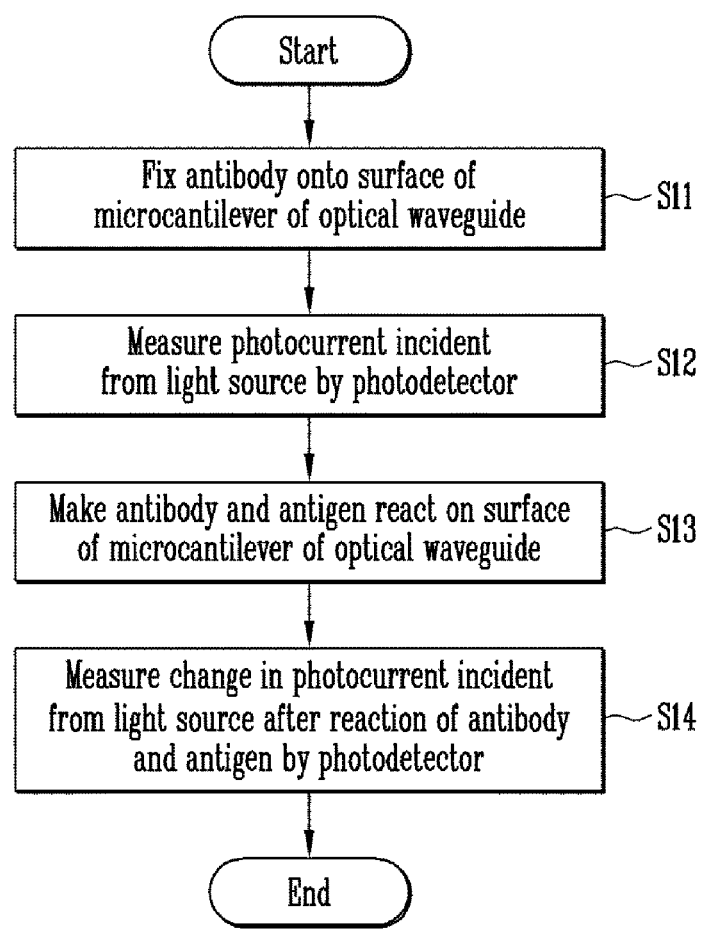

INTEGRAL LABEL-FREE BIOSENSOR AND ANALYSIS METHOD USING THE SAME

CROSS-REFERENCE TO RELATED APPLICATIONS

This application is based on and claims priority from Korean Patent Application Nos. 10-2013-0140105, filed on Nov. 18, 2013 and 10-2014-0032779, filed on Mar. 20, 2014, with the Korean Intellectual Property Office, the disclosure of which is incorporated herein in its entirety by reference.

BACKGROUND

1. Field

The present invention relates to an integral label-free biosensor capable of detecting a biomolecule, and an analysis method using the same, and more particularly, to an integral label-free biosensor, which is capable of qualitatively and quantitatively analyzing a biomolecule by integrally integrating a light source, a photoetector, an optical waveguide, and a microcantilever on a silicon substrate, and an analysis method using the same.

2. Discussion of Related Art

A biosensor is a sensor configured by a bioreceptor and a signal transducer to selectively detect a biomaterial which is to be analyzed.

The bioreceptor includes enzyme, protein, an acceptor, a cell, a tissue, DNA, and the like, which may selectively react to and be selectively combined with a specific biomaterial, and various physiochemical methods, such as an electrochemical method, a fluorescence method, an optical method, a color developing method, and a piezoelectric method, are used as a signal transducing method.

The biosensor is applied to an environment field used for measurement of phenol of waste water, heavy metal, agricultural pesticides, phosphide, and a nitrogen compound, and an analysis of residual agricultural pesticides of food, antibio, and an infectious agent of disease, as well as a sensor field for an early diagnosis or monitoring of various diseases, such as blood sugar, diabetes, cancer, and myocardial infarction, and an application field thereof is a very broad and significant technical field which is up to sensors for military, industry, and research fields.

A signal transducing method used as a method of detecting a biomaterial may be generally divided into two methods, an electrochemical method and an optical method.

The electrochemical method needs to convert a reaction of a biomaterial into a measurable electric signal by using a device, such as an amplifier, in order to detect a minute electric signal generated by a reaction of the biomaterial existing in a sample, such that there is a disadvantage in that equipment and a circuit configuring the biosensor are complex, and used electronic equipment is expensive. Further, since the great number of ions having charges are present in a sample of a body fluid (blood, urine, tear, and the like) including a biomaterial, which is to be analyzed, and the ions have the possibility of influencing an electric signal of the biosensor, the electrochemical method has a limitation in manufacturing a biosensor having excellent selectivity and sensitivity.

By contrast, the optical method is a method of analyzing existence of a biomaterial and a concentration of a biomaterial by converting an optical signal generated from the biomaterial by using a light source and a photodetector, and has an advantage in that it is relatively simple to configure the biosensor and ions having charges existing in a sample less influence an electric signal of the biosensor compared to the electrochemical method, so that the optical method is widely used in a high sensitive biosensor.

In the optical method of detecting a biomaterial in the related art, an optical biosensor for labelling a bio-antibody with a fluorescence material emitting light and the like, detecting a bio-antigen corresponding to the bio-antibody, and calculating the amount of concentration of the bio-antigen, which is to be detected, in proportion to an intensity of fluorescence measured by the biosensor is generally and widely used.

Further, recently, research and development on optical biosensors, such as a surface plasmon biosensor and an optical waveguide biosensor, as a label-free biosensor, which does not use a label material, such as a fluorescence material, has been actively conducted.

The optical biosensor is configured by an external light source for generating light and a photodetector for measuring an optical signal. A laser element is used as the light source for generating light, and a spectrometer is used for detecting an optical signal.

Since the laser device used in the optical biosensor is generally manufactured by using a compound semiconductor thin film, it is difficult to grow a high quality compound semiconductor thin film, and cost for growing a thin film and manufacturing a device is very high. Further, since the compound semiconductor thin film used for manufacturing the light source in the related art is grown on a non-silicon based substrate, it is not easy to integrate the compound semiconductor thin film with a silicon electronic device for configuring a peripheral electronic circuit. Further, since the optical biosensor configures the sensor by using the external light source and the photodetector, the optical biosensor is very complex and requires a precise optical system, and thus there are many disadvantages in that it is difficult to manufacture a small biosensor, mass-produce a biosensor, and manufacture a low-price biosensor.

SUMMARY

For this reason, the inventors studied research for developing an optical biosensor having a simple configuration without an external light source, and found that it is possible to a small, mass-producible, and low-priced biosensor by forming a silicon nano-crystalline light source and a photodetector on a silicon substrate, configuring an optical waveguide connecting a the light source and the photodetector, and configuring a microcantilever on the optical waveguide.

The present invention has been made in an effort to provide an integral label-free biosensor, which is small, has low manufacturing cost, and is very easily integrated with a silicon electronic device for configuring a peripheral circuit, and is capable of easily performing a high sensitive quantitative analysis by integrating a light source itself requiring no external light source, a photodetector, an optical waveguide, and a microcantilever on one silicon substrate.

Further, the present invention has been made in an effort to provide an integral label-free biosensor, which is small, has low manufacturing cost, and is very easily integrated with a silicon electronic device for configuring a peripheral circuit, and is capable of easily performing a high sensitive quantitative analysis by integrating a light source itself requiring no external light source, a photodetector, an optical waveguide, and a microcantilever on one substrate.

An exemplary embodiment of the present invention provides an integral label-free biosensor, including: a substrate; a light source formed on the substrate; a photodetector formed to be spaced apart from the light source on the substrate; a first optical waveguide connected with the light source and extended to the photodetector; a second optical waveguide connected with the photodetector and extended to the light source; an insulating layer formed between the light source and the photodetector on the substrate, and configured to support the first and second optical waveguides; a microcantilever connected to the first optical waveguide, and positioned between the first optical waveguide and the second optical waveguide; and a microfluidic channel configured to inject a sample into the microcantilever.

Another exemplary embodiment of the present invention provides a method of detecting a bio-antigen by using an integral label-free biosensor, including: fixing a bio-antibody onto a microcantilever connected with a first optical waveguide; measuring a photocurrent which is incident into a photodetector from a light source through the first optical waveguide, the microcantilever, and a second optical waveguide; injecting a sample including a bio-antigen through a microfluidic channel, and making the bio-antibody and the bio-antigen react on the microcantilever; and measuring a change in the photocurrent incident to the photodetector from the light source through the first optical waveguide, the microcantilever, and the second optical waveguide after the reaction of the bio-antibody and the bio-antigen.

According to the present invention, it is possible to manufacture the integral label-free biosensor by integrating the light source including silicon nano crystal, the photodetector, the optical waveguide, and the microcantilever. Accordingly, the integral label-free biosensor has low manufacturing cost, and may be very easily integrated with a silicon electron device.

Further, the silicon nano crystalline light source and the photodetector are used, so that an extra external light source and a spectrometer are not required, and further, the optical waveguide and the microcantilever are formed on one substrate, so that it is very easy to configure the integral label-free optical biosensor.

Further, the integral label-free optical biosensor according to the present invention may detect a biomolecule based on protein, DNA, hormone, virus, enzyme, and the like with high sensitivity by using a label-free method, thereby being usable in a qualitative and quantitative analysis.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The above and other features and advantages of the present invention will become more apparent to those of ordinary skill in the art by describing in detail embodiments thereof with reference to the attached drawings in which:

FIG. 4 is a flowchart illustrating a process of detecting a bio-antigen by using the integral label-free biosensor according to the exemplary embodiment of the present invention.

DETAILED DESCRIPTION

Figure 1:
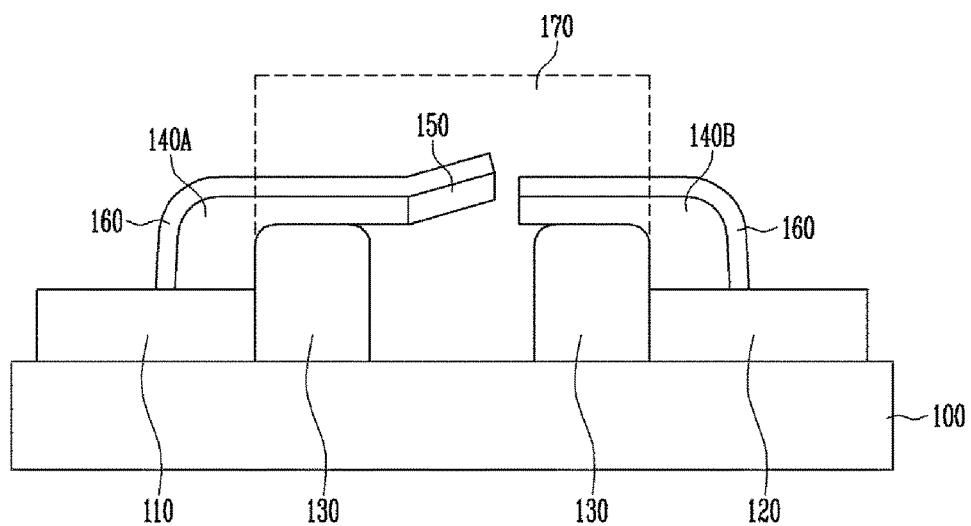
FIG. 1 is a cross-sectional view illustrating an integral label-free biosensor according to an exemplary embodiment of the present invention.

The present invention may have various modifications and various exemplary embodiments and specific exemplary embodiments will be illustrated in the drawings and described in detail in the detailed description. However, it is not intended to limit the present invention to the specific embodiments, and it will be appreciated that the present invention includes all modifications, equivalences, or substitutions included in the spirit and the technical scope of the present invention. In the description of respective drawings, similar reference numerals designate similar elements.

Hereinafter, an exemplary embodiment of the present invention will be described in detail with reference to the accompanying drawings. However, an exemplary embodiment of the present invention, which is to be described below, may be modified into various forms, and the scope of the present invention is not limited to the exemplary embodiment of the present invention, which is to be described below, and may be implemented by various forms. Exemplary embodiments of the present invention are provided so that those skilled in the art may more completely understand the present invention. In the drawings, sizes or thicknesses of layers or regions are exaggerated for clarity of the specification.

FIG. 1 is a cross-sectional view illustrating an integral label-free biosensor according to an exemplary embodiment of the present invention.

Referring to FIG. 1, an integral label-free biosensor according to the present invention includes a substrate 100, a light source 110 formed on the substrate 100, a photodetector 120 formed to be spaced apart from the light source 110 on the substrate 100, a first optical waveguide 140A connected with the light source 110 and extended to the photodetector 120, a second optical waveguide 140B connected with the photodetector 120 and extended to the light source 110, an insulating layer 130 formed between the light source 110 and the photodetector on the substrate 100, and supporting the first and second optical waveguides 140A and 140B, a microcantilever 150 connected to the first optical waveguide 140A to be positioned between the first optical waveguide 140A and the second optical waveguide 140B, and a micro fluidic channel 170 for injecting a sample into the microcantilever 150. Further, the biosensor may further include a polymer layer 160 formed on the first and second optical waveguides 140A and 140B and the microcantilever 150.

The substrate 100 is made of a material which is easily integrated with a silicon electronic device, and may be a silicon substrate. The silicon substrate is cheap, and source gas used for forming the light source 110, the photodetector 120, and the like is cheap. Accordingly, it is possible to reduce manufacturing cost of the label-free biosensor.

The light source 110 and the photodetector 120 are formed on the substrate 100. Here, the light source 110 and the photodetector 120 are positioned to be spaced apart from each other by a predetermined distance. For example, the light source 110 is formed at one side on the substrate 100, and the photodetector 120 is formed on the other side on the same substrate 100.

The light source 100 is a light emitting unit for emitting light. The light detector 120 is a detection unit for absorbing light incident from the light source 100, converting the absorbed light into a current, and detecting the current.

Next, the insulating layer 130 is formed between the light source 110 and the photodetector 120 on the substrate 100. Here, the insulating layer 130 aims to support the first and second optical waveguides 140A and 140B, and may be formed to be higher than the light source 110 and the photodetector 120. For example, the insulating layer 130 may be formed of silicon oxide ($SiO_2$).

Next, the first optical waveguide 140A connected with the light source 110, the microcantilever 150 connected with the first optical waveguide 140A, and the second optical waveguide 140B connected with the photodetector 120 are formed. The first optical waveguide 140A is formed on the light source 110 and the insulating layer 130 to be extended toward the photodetector 120. The second optical waveguide 140B is formed on the photodetector 120 and the insulating layer 130 to be extended toward the light source 110. Further, the microcantilever 150 is connected to the first optical waveguide 140A, and is slantly positioned between the first optical waveguide 140A and the second optical waveguide 140B.

According to the aforementioned structure, the light source 110 and the photodetector 120 may be connected through the first optical waveguide 140A, the microcantilever 150, and the second optical waveguide 140B. For example, light vertically emitted from the light source 110 in an up direction travels along the left-side optical waveguide 140, and then passes through the microcantilever 150 and is incident to the right-side optical waveguide 140. Subsequently, the light vertically travels from the right-side optical waveguide 140 in a down direction to enter the photodetector 120. That is, the first and second optical waveguides 140A and 140B serve to transfer the light incident from the light source 110, and may be formed of silicon nitride ($SiN_x$).

The microcantilever 150 may be integrally connected with the first optical waveguide 140A. That is, a partial region of the first optical waveguide 140A may be used as the microcantilever 150, and the microcantilever 150 may be formed of silicon nitride ($SiN_x$).

For example, the polymer layer 160 is formed on the first and second optical waveguides 140A and 140B, and then the polymer layer 160 is patterned in a finger shape by using electro-beam lithography. Next, when the first and second optical waveguides 140A and 140B are etched by using a chemical etching method, the first and second optical waveguides 140A and 140B are etched in a pattern of the same finger shape as that of the polymer layer 160. Accordingly, the microcantilever 150 may be formed by the partial region of the first optical waveguide 140A by patterning the first optical waveguide 140A. In this case, the microcantilever 150 is formed by etching the silicon nitride ($SiN_x$) used as the polymer layer 160 and the optical waveguide 140, so that the silicon nitride ($SiN_x$) optical waveguide 140 and polymer layer 160 structurally form the microcantilever 150.

Next, a microfluidic channel 170 is formed on the first optical waveguide 140A, the microcantilever 150, and the second optical waveguide 140B. The channel 170 aims to inject a sample, such as a body fluid (blood, urine, tear, and the like) including a bio-antigen.

A bio-antibody is fired on the microcantilever 150 or the polymer layer 160. Accordingly, when the bio-antibody fixed to the microcantilever 150 reacts to the bio-antigen flowing in through the microfluidic channel 170, the microcantilever 150 moves to connect the left-side first optical waveguide 140A and the right-side second optical waveguide 140B. Next, the light emitted from the light source 110 is incident to the photodetector 120 through the first optical waveguide 140a, the microcantilever 150, and the second optical waveguide 140b to be converted into a photocurrent.

In this case, there is a difference in the photocurrent before and after the reaction of the bio-antibody and the bio-antigen. Accordingly, when the difference in the photocurrent is analyzed, it is possible to recognize whether a desired biomaterial, that is, the bio-antigen, exists, and quantitatively analyze a concentration of the bio-antigen.

For reference, the antibody may be fixed onto the second optical waveguide 140b or the polymer layer 160 formed on the second optical waveguide 140b.

Figure 2:
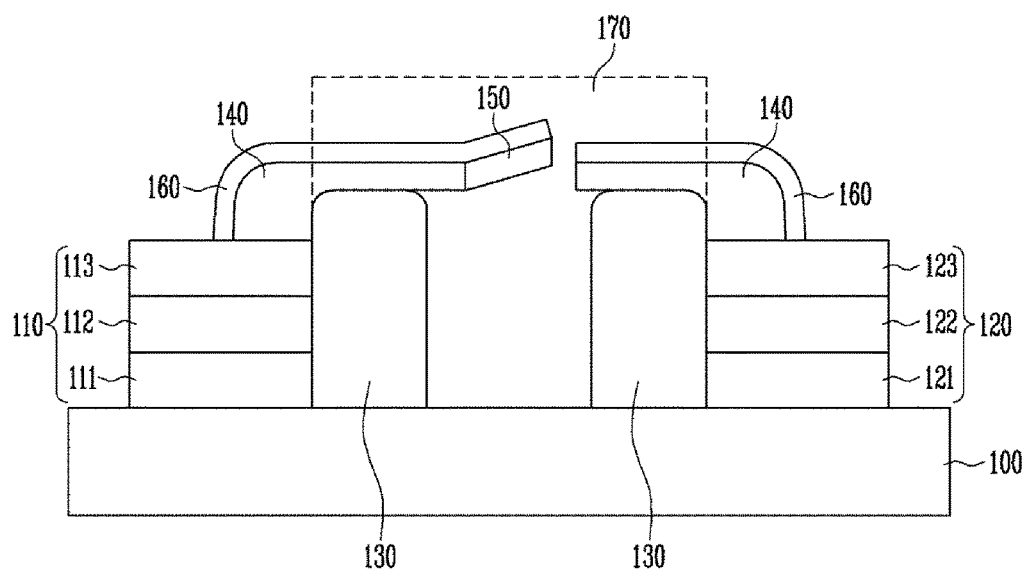
FIG. 2 is a cross-sectional view illustrating an integral label-free biosensor according to another exemplary embodiment of the present invention.

FIG. 2 is a cross-sectional view illustrating an integral label-free biosensor according to another exemplary embodiment of the present invention.

Referring to FIG. 2, according to a configuration of the biosensor according to the present invention, similar to FIG. 1, a light source 110 is formed on one side surface of an upper part of a substrate 100, and a photodetector 120 is formed on another side surface of the upper part of the substrate 100.

The light source 110 may include a hole injection layer 111, a light emitting layer 112, and an electron injection layer 113 formed on the silicon substrate 100. The hole injection layer 111 is a layer for injecting holes into the light emission layer 112, and may be formed of a thin film selected from the group consisting of a p-type silicon thin film, a p-type silicon carbide-based thin film, and a silicon carbon nitride-based thin film. The light emission layer 112 formed on the hole injection layer 111 is a layer for emitting light by combining electrons and holes. For example, the silicon nano-crystalline emission layer 112 may be formed by using a silicon carbide (SiC) thin film including silicon nano crystal. The electron injection layer 113 on the light emission layer 112 is a layer for injecting electrons into the light emission layer 112. For example, the electron injection layer 113 is formed of an n-type silicon carbide-based thin film or a silicon carbon nitride-based thin film.

The photodetector 120 includes a hole doping layer 121, a light separation layer 112, and an electron doping layer 123. The hole doping layer 121 may be formed of a thin film selected from the group consisting of p-type silicon, a p-type silicon carbide-based tin film, and a silicon carbon nitride-based thin film. The light separation layer 122 formed on the hole doping layer 121 separates light absorbed from the light source 100, which emits light itself, into electrons and holes. For example, the light separation layer 122 is formed by using a silicon carbide (SiC) thin film including silicon nano-crystal. The electron doping layer 123 formed on the light separation layer 122 may be formed of an n-type silicon carbide-based thin film or a silicon carbon nitride-based thin film.

Next, an insulating layer 130 is formed between the light source 110 and the photodetector 120 on the substrate 100. Here, the insulating layer 130 may be formed of silicon oxide ($SiO_2$).

Next, the light source 110 and the photodetector 120 are configured to be connected through an optical waveguide 140 formed on the insulating layer 130. Here, the optical waveguide 140 is formed by using a silicon nitride ($SiN_x$) thin film. A microcantilever 150 may be formed by etching a predetermined region of the optical waveguide 140 by using a chemical etching method.

In the light source 110 and the photodetector 120 of the label-free biosensor according to the present invention, the hole injection layer/the hole doping layer 111 and 121 and the electron injection layer/the electron doping layer 113 and 123 are formed to face each other while having the light emission layer/the thin film layer 112 and 122 including the silicon nano crystal interposed therebetween. Further, the light source 110 and the photodetector 120 of the biosensor according to the present invention make light enter the optical waveguide 140 by applying voltages in different directions through an external electrode, and measure a difference in a value of a photocurrent through a reaction of a bio-antibody and a bio-antigen incurred in the region of the microcantilever 150 formed on the surface of the optical waveguide 140.

A polymer layer 160 may be formed on the regions of the optical waveguide 140 and the microcantilever 150. Further, a microfluidic channel 170 is formed on the microcantilever 150 and the optical waveguide 140. The microfluidic channel 170 may be formed by using silicon, an organic material, or PDMS.

Figure 3A:
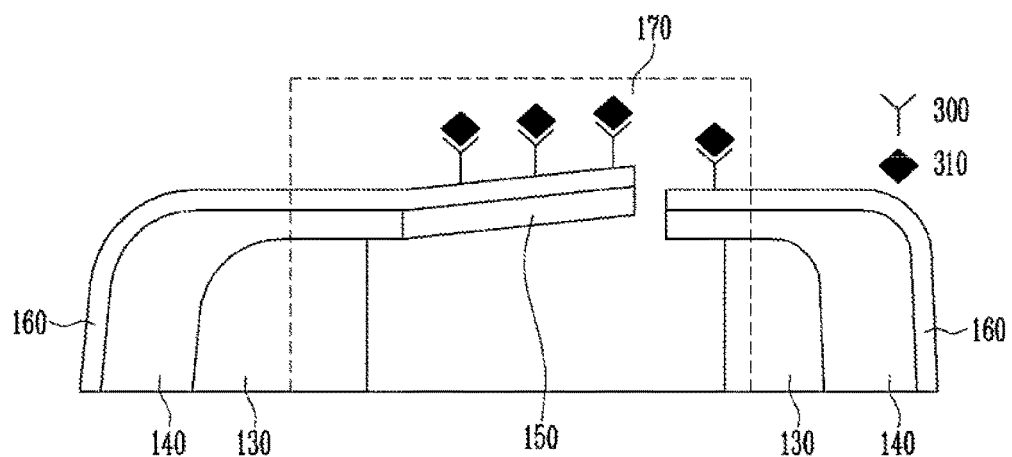
FIGS. 3A and 3B are schematic diagrams illustrating a configuration and a detection principle of a micro fluidic channel formed on a microcantilever and an optical waveguide of the biosensor of FIG. 2.
Figure 3B:
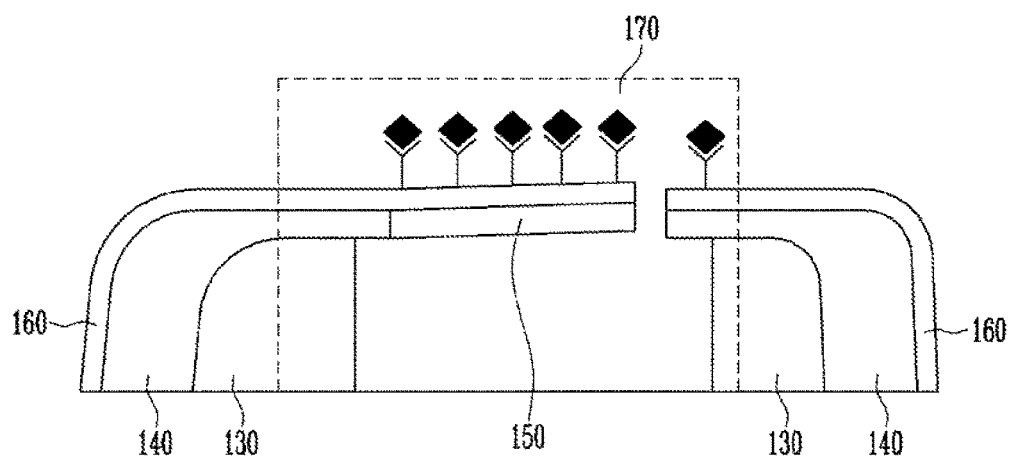

FIGS. 3A and 3B are schematic diagrams illustrating a detection principle of the biosensor according to an exemplary embodiment of the present invention, and particularly, a principle of quantitatively detecting a concentration of the bio-antigen.

As illustrated in FIGS. 3A and 3B, when a sample including a bio-antigen 310 is injected through the microfluidic channel 170, the bio-antigen 310 is fixed to an anti-body 300 fixed to the polymer layer 160 on the microcantilever 150.

In this case, the optical waveguide 140 is supported by the insulating layer 130, so that the optical waveguide 140 does not move even though the bio-antigen 310 is combined with the bio-antibody 300. By contrast, the microcantilever 150 is not supported by the insulating layer 130, so that when the bio-antibody 300 is fixed to the bio-antigen 310, the microcantilever 150 moves downwardly due to mass of the bio-antigen 300. Accordingly, the microcantilever 150 and the right-side optical waveguide 150 are close to each other, and thus a photocurrent is changed.

FIGS. 3A and 3B illustrate a difference in a gradient of the microcantilever 150 according to a concentration difference of the bio-antigen 310. FIG. 3A illustrates the case where the concentration of the bio-antigen 310 fixed to the bio-antibody 300 is relatively low, and FIG. 3B illustrates the case where the concentration of the bio-antigen 310 fixed to the bio-antibody 300 is relatively high. As the concentration of the bio-antigen 310 fixed to the bio-antibody 300 is increased, the microcantilever 150 moves downwardly more due to mass of the bio-antigen 310.

As the microcantilever 150 moves downwardly more, a distance between the microcantilever 150 and the right-side optical waveguide 140 is decreased, so that the photocurrent is also further increased. Accordingly, it is possible to quantitatively detect the concentration of the bio-antigen 310 fixed to the microcantilever 150 by analyzing a difference in the photocurrent through the photodetector 120.

FIG. 4 is a flowchart illustrating a process of detecting a bio-antigen by using the biosensor of FIG. 2.

Referring to FIG. 4, a method of detecting a bio-antigen by the biosensor according to the present invention includes: operation S11 of fixing an antibody onto a surface of the microcantilever of the optical waveguide 140; operation S12 of measuring, by the photodetector 120, a photocurrent which is incident from the light source 110 through the optical waveguide 140; operation S13 of making an antibody and the antigen react on the surface of the microcantilever 150 of the optical waveguide 140; and operation S14 of measuring, by the photodetector 120, a change in the photocurrent, which is incident from the light source 110 through the optical waveguide 140 after the reaction of the antibody and the antigen.

This will be described in detail. First, the bio-antibody 300 is fixed onto the surface of the microcantilever 150 formed on the predetermined region of the optical waveguide 140 by using a chemical, physical, or biological method. In this case, the bio-antibody 300 may be fixed onto a surface of the polymer layer 160 on the microcantilever 150. Next, the photodetector 120 measures the photocurrent incident from the light source 110. Next, when a body fluid (blood, urine, tear, and the like) flows through the microfluidic channel 170, the bio-antibody 300 fixed to the region of the microcantilever 150 and the bio-antigen 310 existing in the body fluid react with each other to be combined. Accordingly, an inclination of the microcantilever 150 is changed. After the reaction of the antibody and the antigen, the photodetector 120 measures the photocurrent again. Accordingly, it is possible to confirm that the photocurrent before the reaction of the bio-antibody 300 and the bio-antigen 310 is different from the photocurrent after the reaction of the bio-antibody 300 and the bio-antigen 310, and it is possible to detect the bio-antigen 310, which is to be analyzed, by using the principle.

As described above, the embodiment has been disclosed in the drawings and the specification. The specific terms used herein are for purposes of illustration, and do not limit the scope of the present invention defined in the claims. Accordingly, those skilled in the art will appreciate that various modifications and another equivalent example may be made without departing from the scope and spirit of the present disclosure. Therefore, the sole technical protection scope of the present invention will be defined by the technical spirit of the accompanying claims.

What is claimed is:

1. An integral label-free biosensor, comprising:
a substrate;
a light source disposed on the substrate;
a photodetector disposed on the substrate and spaced apart from the light source;
a first optical waveguide connected with the light source, the first optical waveguide extending toward the photodetector;
a second optical waveguide connected with the photodetector, the second optical waveguide extending toward the light source;
an insulating layer disposed between the light source and the substrate, and between the photodetector and the substrate, the insulating layer supporting the first and second optical waveguides;
a microcantilever connected to the first optical waveguide, the microcantilever extending toward the second optical waveguide and being configured to move with respect to the second optical waveguide;
a bio antibody fixed on the microcantilever; and
a microfluidic channel configured to provide a sample onto the microcantilever.

2. The integral label-free biosensor of claim 1, further comprising:
a polymer layer disposed on the first optical waveguide, the microcantilever, and the second optical waveguide.

3. The integral label-free biosensor of claim 2, wherein a bio-antibody is fixed onto the polymer layer.

4. The integral label-free biosensor of claim 1, wherein the first optical waveguide and the microcantilever are integrally connected.

5. The integral label-free biosensor of claim 1, wherein the microfluidic channel is positioned over the microcantilever, the first optical waveguide, and the second optical waveguide.

6. The integral label-free biosensor of claim 1, wherein the light source includes a hole injection layer, a light emission layer, and an electron injection layer, which are sequentially stacked.

7. The integral label-free biosensor of claim 6, wherein the light emission layer comprises silicon nitride including a silicon nano crystal,
   wherein the hole injection layer includes a material selected from the group consisting of a p-type silicon thin film, a p-type silicon carbide-based thin film, and a silicon carbon nitride-based thin film, and
   wherein the electron injection layer includes a material selected from an n-type silicon carbide-based thin film and a silicon carbon nitride-based thin film.

8. The integral label-free biosensor of claim 1, wherein the photodetector includes a hole doping layer, a light separation layer, and an electron doping layer, which are sequentially stacked.

9. The integral label-free biosensor of claim 8, wherein the light separation layer comprises silicon nitride including a silicon nano crystal,
   wherein the hole doping layer includes a material selected from the group consisting of a p-type silicon thin film, a p-type silicon carbide-based thin film, and a silicon carbon nitride-based thin film, and
   wherein the electron doping layer includes a material selected from an n-type silicon carbide-based thin film and a silicon carbon nitride-based thin film.

10. The integral label-free biosensor of claim 1, wherein the insulating layer is a silicon oxide ($SiO_2$) thin film.

11. The integral label-free biosensor of claim 1, wherein the optical waveguide is a silicon nitride ($SiN_x$) thin film.

12. A method of detecting a bio-antigen by using the integral label-free biosensor of claim 1, the method comprising:
   fixing a bio-antibody onto a microcantilever connected with a first optical waveguide and disconnected from a second optical waveguide;
   measuring a photocurrent based on light incident onto a photodetector, the light being generated by a light source and passing through the first optical waveguide, the microcantilever, and the second optical waveguide;
   injecting a sample through a microfluidic channel, where when the sample includes a bio-antigen, the bio-antibody and the bio-antigen react on the microcantilever and a weight of the reacted bio-antibody and bio-antigen move the microcantilever toward the second optical waveguide; and
   measuring a change in the photocurrent after the sample has been injected through the microfluidic channel.

13. The integral label-free biosensor of claim 1, wherein the microcantilever is spaced apart from the second optical waveguide by a first distance when the bio-antibody is unattached to a bio-antigen, and
   wherein the microcantilever is spaced apart from the second optical waveguide by a second distance when the bio-antibody is attached to the bio-antigen, the second distance being shorter than the first distance.

14. The integral label-free biosensor of claim 1, wherein the photodetector detects light transmitted from the light source and through the first optical waveguide, the microcantilever, and the second optical waveguide.

15. An apparatus, comprising:
   a light source emitting light;
   a first optical waveguide optically coupled to the light source and configured to transmit the light emitted from the light source;
   a microcantilever configured to transmit the light from the first optical waveguide, the microcantilever being fixed to the first optical waveguide;
   a second optical waveguide configured to transmit the light from the microcantilever, the microcantilever being disconnected from the second optical waveguide;
   an antibody attached to the microcantilever, the microcantilever moving toward the second optical waveguide when the antibody reacts with an antigen; and
   a photodetector optically coupled to the second optical waveguide, the photodetector receiving the light transmitted through the second optical waveguide.

16. The apparatus of claim 15, wherein the microcantilever is spaced apart from the second optical waveguide by a first distance when the antibody is unattached to the antigen, and
   wherein the microcantilever is spaced apart from the second optical waveguide by a second distance when the antibody is attached to the antigen, the second distance being shorter than the first distance.

17. The apparatus of claim 15, further comprising:
   a microfluidic channel positioned over the microcantilever, the first optical waveguide, and the second optical waveguide.

18. The apparatus of claim 15, wherein the light source includes a hole injection layer, a light emission layer, and an electron injection layer, which are sequentially stacked.

19. The apparatus of claim 18, wherein the light emission layer comprises silicon nitride including a silicon nano crystal,
   wherein the hole injection layer includes a material selected from the group consisting of a p-type silicon thin film, a p-type silicon carbide-based thin film, and a silicon carbon nitride-based thin film, and
   wherein the electron injection layer includes a material selected from an n-type silicon carbide-based thin film and a silicon carbon nitride-based thin film.

20. The apparatus of claim 15, wherein the photodetector includes a hole doping layer, a light separation layer, and an electron doping layer, which are sequentially stacked.

* * * * *